United States Patent [19]

Hao et al.

[11] Patent Number: 5,646,299
[45] Date of Patent: Jul. 8, 1997

[54] TWO NEW CRYSTAL MODIFICATIONS OF A DIKETOPYRROLOPYRROLE PIGMENT

[75] Inventors: Zhimin Hao, Marly; Abul Iqbal, Arconciel; Fritz Herren, Düdingen, all of Switzerland

[73] Assignee: Ciba-Geigy Corporation, Tarrytown, N.Y.

[21] Appl. No.: 493,776

[22] Filed: Jun. 22, 1995

[30] Foreign Application Priority Data

Jun. 29, 1994 [CH] Switzerland .............. 2076/94

[51] Int. Cl.$^6$ .................. C01D 487/06
[52] U.S. Cl. .................. 548/453
[58] Field of Search .................. 548/453

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,666,455 | 5/1987 | Jost et al. | 8/506 |
| 4,778,899 | 10/1988 | Pfenninger et al. | 548/453 |
| 4,783,540 | 11/1988 | Babler | 548/453 |
| 4,931,566 | 6/1990 | Surber et al. | 548/453 |
| 5,223,624 | 6/1993 | Babler et al. | 546/49 |
| 5,476,949 | 12/1995 | Wallquist et al. | 548/453 |
| 5,484,943 | 1/1996 | Zambounis et al. | 548/453 |
| 5,502,208 | 3/1996 | Wallquist | 548/453 |

FOREIGN PATENT DOCUMENTS 0061426  9/1982  European Pat. Off. .

OTHER PUBLICATIONS

Mizuguhci, J., Chimia, 48(9), 439–42 1994.
Mizuguchi, et al., Ber. Bunsen–Ges. Phys. Chem., 96(4), 597–606 1992.
J. Mizuguchi et al., Acta Crystallographica, vol. 348, Part 5, pp. 696–700, (1992).
Herbst et al., Industrial Organic Pigments, pp. 41–43, 427–428 and 453–454 (1993).
Angew. Chem. Int. Ed. Engl., vol. 28, (1989), No. 4, pp. 478–480.

*Primary Examiner*—Johann Richter
*Assistant Examiner*—Laura R. Cross
*Attorney, Agent, or Firm*—Michele A. Kovaleski; David R. Crichton

[57] ABSTRACT

Diketopyrrolopyrrole of the formula in its β-modification and in its γ-modification.

Both the β-modification and the γ-modification are suitable as pigments for coloring high-molecular weight organic material. In comparison to the α-modification, the β-modification shows a shift in shade towards yellowish-red. The γ-modification gives brilliant orange colorations.

2 Claims, No Drawings

TWO NEW CRYSTAL MODIFICATIONS OF A DIKETOPYRROLOPYRROLE PIGMENT

The present application relates to two new crystal modifications (β and γ) of 1,4-diketo-3,6-bis(3-methylphenyl)pyrrolo[3,4-c]pyrrole, to their preparation and the use of these new products as pigments.

It is general knowledge that a number of representatives of different classes of organic pigments are polymorphous. Despite having the same chemical composition, such pigments occur in two or more crystal modifications. This is the case in particular for phthalocyanine, quinacridone and some azo pigments (cf. e.g. W. Herbst, K. Hunger, Industrial Organic Pigments (1993), 41–43, 427–428, 453–454). For some other pigments, in contrast, only one single crystal modification is known. For instance, despite a number of attempts it has hitherto been impossible to obtain, for any one of the diketopyrrolopyrrole pigments, which have been known for some years and are described, for example, in U.S. Pat. Nos. 4 415 685 and 4 579 949, a second crystal modification.

It has recently been found that leaving groups, for example those of the formula

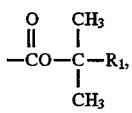

in which $R_1$ is $C_1$–$C_6$alkyl, can be introduced readily even into insoluble substances, like the diketopyrrolopyrrole pigments, with formation of soluble carbamates having the basic structure

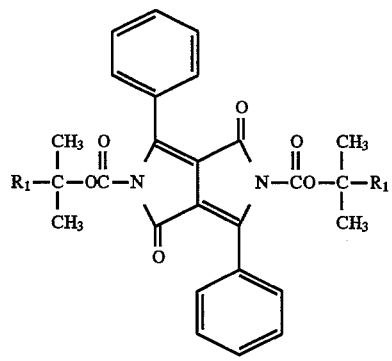

and that, by thermal (heating to temperatures of between 50° and 400° C.), chemical (with organic or inorganic acids or bases) or photolytic (exposure with, for example, wavelengths below 375 nm) treatment the original pigment can be reformed. These studies are described in U.S. Pat. No. 5,484,943.

Astonishingly it has now been found that, in the case of the diketopyrrolopyrrole of the formula

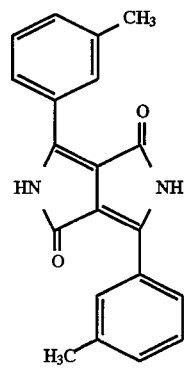

the abovementioned reformation of the (N-unsubstituted) pigment by chemical or, respectively, by thermal treatment under specific conditions leads not to the previously known modification but in each case to a new crystal modification.

The new modification obtained by chemical treatment, i.e. by heating at from 80° to 120° C. in an aprotic organic solvent in the presence of an acid, referred to hereinafter as the β-modification, and that obtained by thermal treatment, i.e. by dry heating at from 200° to 350° C., referred to hereinafter as the γ-modification, differ from one another and from the known modification, referred to hereinafter as the α-modification, by a specific, different X-ray diffraction pattern. The β-modification moreover, which is transformed again into the α-modification on heating at temperatures which vary depending on the substrate, displays, in comparison to the red α-modification, a shift in shade towards yellowish-red, whereas the heat-stable γ-modification is characterized by a brilliant orange shade.

The complete X-ray diffraction patterns are determined by conventional methods using a Siemens D500® X-ray diffractometer ($CuK_\alpha$ radiation).

The X-ray diffraction pattern of the known α-modification is characterized by the following diffraction lines

| Interplanar spacings (d values in Å) | double glancing angle (2Θ) | relative intensity |
| --- | --- | --- |
| 13.7152 | 6.44 | 100 |
| 5.5783 | 15.88 | 46 |
| 5.1540 | 17.19 | 8 |
| 4.9920 | 17.75 | 10 |
| 4.7200 | 18.79 | 12 |
| 4.5354 | 19.56 | 30 |
| 4.3219 | 20.53 | 9 |
| 4.0783 | 21.77 | 23 |
| 3.6239 | 24.55 | 26 |
| 3.5186 | 25.29 | 22 |
| 3.3036 | 26.97 | 96 |

The present invention relates to the diketopyrrolopyrrole of the formula a) in its β-modification, whose X-ray diffraction pattern is characterized by the following diffraction lines

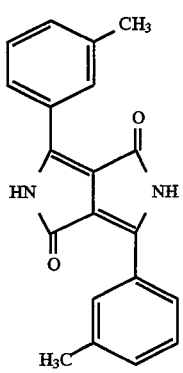

| Interplanar spacings (d values in (Å) | double glancing angle (2Θ) | relative intensity |
|---|---|---|
| 13.7172 | 6.44 | 100 |
| 5.4273 | 16.32 | 44 |
| 4.7045 | 18.85 | 18 |
| 4.5517 | 19.49 | 31 |
| 4.3463 | 20.42 | 22 |
| 4.1056 | 21.63 | 11 |
| 3.4241 | 26.00 | 70 |
| 3.2844 | 27.13 | 31 |
| 3.0960 | 28.81 | 16 |
| 3.0625 | 29.14 | 18 | and
b) in its γ-modification, whose X-ray diffraction pattern is characterized by the following diffraction lines

| Interplanar spacing (d values in Å) | double glancing angle (2Θ) | relative intensity |
|---|---|---|
| 11.1386 | 7.93 | 100 |
| 6.9644 | 12.70 | 19 |
| 4.6733 | 18.98 | 10 |
| 4.3887 | 20.22 | 12 |
| 4.0033 | 22.19 | 19 |
| 3.6052 | 24.67 | 84 |
| 3.3749 | 26.39 | 12 |
| 3.2335 | 27.56 | 49 |
| 2.9053 | 30.75 | 13 |

The γ-modification is preferred.

The new β-modification is prepared by dissolving a soluble diketopyrrolopyrrole of the formula

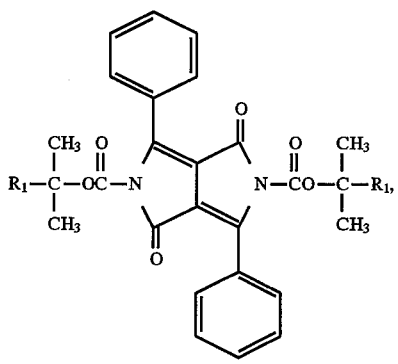

in which $R_1$ is $C_1$–$C_6$alkyl, in an organic solvent, heating the solution at a temperature of between 80° and 120° C. in the presence of an acid, and then isolating the product, which has precipitated after cooling, by conventional methods.

$R_1$ as $C_1$–$C_6$alkyl is for example methyl, ethyl, n-propyl, isopropyl, n-butyl, ten-butyl, n-amyl or hexyl.

$R_1$ is preferably ethyl, but especially methyl.

The dissolved diketopyrrolopyrrole of the formula II is advantageously treated in the presence of the acid under reflux for from 5 to 60 minutes, depending on the solvent, and the mixture is then advantageously cooled to from 10° to 30° C.

Solvents which can be used are inert aprotic organic solvents, for example dimethylformamide, tetrahydrofuran, ethylene glycol, ethylene glycol monomethyl ether, dodecane, toluene, xylene, acetylacetone, dimethyl sulfoxide or mixtures thereof. Preference is given to dimethyl sulfoxide, acetylacetone, ethylene glycol monomethyl ether and, in particular, dimethylformamide.

Suitable acids are both inorganic and organic acids, for example hydrochloric acid, sulfuric acid, toluenesulfonic acid or trifluoroacetic acid. 4-Toluenesulfonic acid is preferred. It is advantageous to employ from 8 to 30, preferably from 15 to 20 mol, of acid per mole of diketopyrrolopyrrole of the formula II. The acid can be added either before, together with or after the pigment salt suspension, preferably before or together with the pigment salt suspension.

It is preferred to use from 15 to 20 mol of 4-toluenesulfonic acid, based on the diketopyrrolopyrrole, in N,N-dirnethylformamide at from 100° to 105° C. for from 15 to 20 minutes.

The new γ-modification is prepared by heating a diketopyrrolopyrrole of the formula

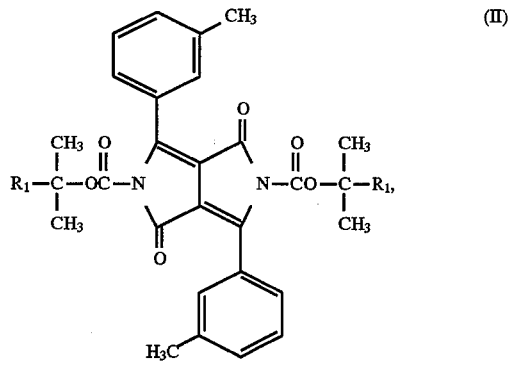

in which $R_1$ is $C_1$–$C_{16}$ alkyl, at a temperature of from 200° to 350° C. for from 10 minutes to 10 hours.

The diketopyrrolopyrrole of the formula II is preferably heated in powder form at from to 260° C. for from 30 minutes to 2 hours.

Diketopyrrolopyrroles of the formula II can be obtained in analogy to generally known methods, for example by reacting a diketopyrrolopyrrole of the formula I with a dicarbonate of the formula

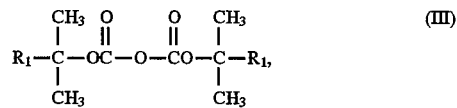

or with a trihaloacetic ester of the formula

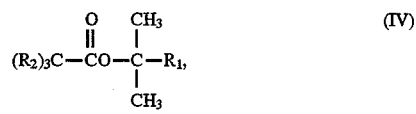

in which $R_2$ is chlorine, fluorine or bromine, or with an azide of the formula

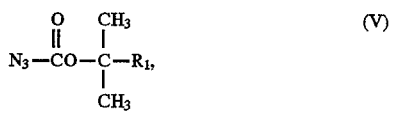

R₁ being in each case as defined above,
in an aprotic organic solvent in the presence of a base as catalyst at temperatures of between 0° and 400° C. for from 2 to 80 hours.

The dicarbonate of the formula III, the trihaloacetic ester of the formula IV or the azide of the formula V is advantageously employed in a from 2- to 10-fold excess.

The diketopyrrolopyrrole of the formula I is preferably reacted with a dicarbonate of the formula III.

Dicarbonates of the formula III, trihaloacetic esters of the formula IV and azides of the formula V are known substances. Any that may be novel can be prepared in analogy to generally known methods.

Examples of suitable solvents are ethers, such as tetrahydrofuran or dioxane, or glycol ethers, such as ethylene glycol methyl ether, ethylene glycol ethyl ether, diethylene glycol monomethyl ether or diethylene glycol monoethyl ether, dipolar aprotic solvents, such as acetonitrile, benzonitrile, N,N-dimethylformamide, N,N-dimethylacetamide, nitrobenzene or N-methylpyrrolidone, halogenated aliphatic or aromatic hydrocarbons, such as trichloroethane, benzene or alkyl-, alkoxy- or halogen-substituted benzene, such as toluene, xylene, anisole or chlorbenzene, or aromatic nitrogen heterocycles, such as pyridine, picoline or quinoline. Examples of preferred solvents are tetrahydrofuran, N,N-dimethylformamide and N-methylpyrrolidone. The solvents mentioned may also be employed as mixtures. It is advantageous to use from 5 to 20 parts by weight of solvent per part by weight of the reactants.

Examples of bases which are suitable as catalysts are the alkali metals themselves, such as lithium, sodium or potassium and their hydroxides or carbonates, or alkali metal amides, such as lithium amide, sodium amide or potassium amide, or alkali metal hydrides, such as lithium hydride, sodium hydride or potassium hydride, or alkaline earth metal or alkali metal alcoholates which are derived, in particular, from primary, secondary or tertiary aliphatic alcohols of 1 to 10 carbon atoms, for example lithium, sodium or potassium methylate, ethylam, n-propylate, isopropylate, n-butylate, sec-butylate, tert-butylate, 2-methyl-2-butylate, 2-methyl-2-pentylate, 3-methyl-3-pentylate or 3-ethyl-3-pentylate, and also organic aliphatic, aromatic or heterocyclic nitrogen bases, including for example diazabicyclooctane, diazabicycloundecene and 4-dimethylaminopyridine, and trialkylamines, for example trimethylamine or triethylamine. It is also possible to use a mixture of the bases mentioned.

Preference is given to the organic nitrogen bases such as, for example, diazabicyclooctane, diazabicycloundecene and, in particular, 4-dimethylaminopyridine.

The reaction is preferably carried out at temperatures of between 10° and 100° C., in particular between 14° and 40° C., and at atmospheric pressure.

The β- and γ-diketopyrrolopyrroles of the invention are also suitable, as already described, for example in U.S. Pat. Nos. 4 415 685 and 4 579 949 for their α-modification, as pigments for colouring high molecular weight organic material. However, since the β-diketopyrrolopyrrole is transformed again into the α-modification on heating at temperatures which vary depending on the substrate, its use in materials which are processed at relatively high temperatures requires caution to be exercised. The γ-diketopyrrolopyrrole, in contrast, is very stable and is highly suitable for use even in high molecular weight materials such as, for example polyolefins and polyesters, having very high saturation.

Like many other pigments, the β- and γ-diketopyrrolopyrroles according to the invention can also be advantageously surface-treated by known methods in order to improve their properties in coating systems. Additives which are employed to reduce or avoid flocculation and to improve the dispersion stability can be used advantageously with the pigments according to the invention. The pigments treated in this way exhibit good properties, alone or mixed with other pigments, for the production of red to orange masstone colorations in a variety of coating systems, but preferably in automotive finishing systems of the acrylic, alkyd and polyester type. 2-Phthalimidomethylquinacridone, quinacridonesulfonic acid and other similar derivatives are examples of deflocculating agents which can be used. In certain systems, the addition of polymeric dispersants may bring about an additional improvement in the properties of the pigments.

The β- and γ-diketopyrrolopyrroles according to the invention are employed in quantities of from 0.01 to 30% by weight, preferably from 0.1 to 10% by weight, based on the high molecular weight organic material to be coloured, and are incorporated into this material advantageously at temperatures between 20° and 180° C. for the β-form and at between 20° and 300° C. for the γ-diketopyrrolopyrrole.

The β- and γ-diketopyrrolopyrroles according to the invention can be employed, for example, as a powder, paste, flush paste or formulation and are suitable, for example, for printing inks, sizing colours, binder colours or coatings of all kinds, such as physically and oxidatively drying coating materials, acid-, amine- and peroxide-curing coating materials or polyurethane coating materials. Depending on their compatibility with the processing temperature, the pigments according to the invention can also be used for colouring synthetic, semisynthetic or natural macromolecular substances, such as polyvinyl chloride, polystyrene, polyethylene, polypropylene, polyesters, phenolic resins, amino resins and rubber. Examples of further applications are the colouring of natural, regenerated or synthetic fibres, such as fibres of glass, silicate, asbestos, wood, cellulose, acetylcellulose, polyacrylonitrile, polyester, polyurethane and polyvinyl chloride or mixtures of these fibres, alone or together with other organic or inorganic pigments. The resulting colorations, for example in coating materials, prints or plastics, are distinguished by a yellowish-red to orange colour, good fastness to overspraying, migration, light and weathering, and by high tinctorial strength and transparency.

The pigments according to the invention can be used for colouring solid, elastic, pastelike, high-viscosity, low-viscosity or thixotropic materials and can be incorporated into these materials by methods which are known per se. For example, water-containing pastes can be obtained by stirring the pigment into water, with or without the addition of a wetting agent or dispersant, or by stirring or kneading the pigment into a dispersant in the presence of water and in the presence or absence of organic solvents or oils. These pastes can be employed in turn, for example, to produce flush pastes, printing inks, sizing colours and polymer dispersions. However, the pigment can also be introduced by stirring, rolling, kneading or grinding into water, organic solvents, non-drying oils, drying oils, coating materials, plastics or rubber. Finally, it is also possible to process the pigment by dry mixing with organic or inorganic materials, granules, fibrous substances, powders and other pigments, to give compositions.

The examples which follow illustrate the invention.

Example 1a: (Preparation of the soluble diketopyrrolopyrrole)

15.2 g of di-tert-butyl dicarbonate are added to a mixture of 10.0 g of 1,4-diketo-3,6-di-(3-methylphenyl)pyrrolo[3,4- c]pyrrole and 1.0 g of 4-dimethylaminopyridine in 350 ml of tetrahydrofuran (dried over molecular sieve). The resulting orange suspension is stirred at room temperature for 20 hours with the exclusion of atmospheric moisture. The solvent is then distilled off under reduced pressure. The brown residue is washed first with water and then with methanol and is dried in vacuo at room temperature, to give 14.1 g (86.5% of theory) of a bright yellow product of the formula

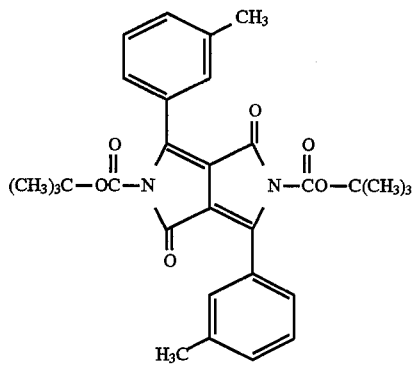

| Analysis: | C | H | N |
|---|---|---|---|
| calc.: | 69.75% | 6.24% | 5.42% |
| found: | 69.82% | 6.40% | 5.47% | b) 7.4 g of 4-toluenesulfonic acid are added to a solution of 1.0 g of the product from a) in 75 ml of N,N-dimethylformamide. The mixture is heated to 100° C., stirred at this temperature for 15 minutes, and then cooled suddenly in an ice bath to 20° C. The precipitated pigment is filtered off, washed with methanol and then with water, and dried in vacuo at 60° C., to give 0.43 g of a red powder.

| Analysis: | C | H | N |
|---|---|---|---|
| calc.: | 75.93% | 5.10% | 8.86% |
| found: | 75.91% | 5.14% | 8.69% |

The X-ray diffraction pattern is characterized by the following diffraction lines

| Interplanar spacing (d values in Å) | double glancing angle (2Θ) | relative intensity |
|---|---|---|
| 13.7172 | 6.44 | 100 |
| 5.4273 | 16.32 | 44 |
| 4.7045 | 18.85 | 18 |
| 4.5517 | 19.49 | 31 |
| 4.3463 | 20.42 | 22 |
| 4.1056 | 21.63 | 11 |
| 3.4241 | 26.00 | 70 |
| 3.2844 | 27.13 | 31 |
| 3.0960 | 28.81 | 16 |
| 3.0625 | 29.14 | 18 |

Example 2: 2.3 g of the product from Example 1a are placed in a crystallizing dish, then introduced into an oven preheated to 240° C., and are held at this temperature for one hour. The product is then allowed to cool to room temperature, to give 1.3 g of an orange powder which, when incorporated into PVC, gives a brilliant orange coloration.

| Analysis: | C | H | N |
|---|---|---|---|
| calc.: | 75.93% | 5.10% | 8.86% |
| found: | 75.75% | 5.09% | 8.86% |

The X-ray diffraction pattern is characterized by the following diffraction lines

| Interplanar spacing (d values in Å) | double glancing angle (2Θ) | relative intensity |
|---|---|---|
| 11.1386 | 7.93 | 100 |
| 6.9644 | 12.70 | 19 |
| 4.6733 | 18.98 | 10 |
| 4.3887 | 20.22 | 12 |
| 4.0033 | 22.19 | 19 |
| 3.6052 | 24.67 | 84 |
| 3.3749 | 26.39 | 12 |
| 3.2335 | 27.56 | 49 |
| 2.9053 | 30.75 | 13 |

Example 3: 7.5 g of the pigment whose preparation is described in Example 1b, 98.9 g of CAB solution comprising

| 41.00 g | of cellulose acetobutyrate ® CAB 531.1, 20% in 2:1 butanol/xylene (Eastman Chem.) |
| 1.50 g | of zirconium octoate |
| 18.50 g | of ® SOLVESSO 150* |
| 21.50 g | of butyl acetate and |
| 17.50 g | of xylene |
| 36.50 g | of polyester resin ® DINAPOL H700 (Dynamit Nobel), 4.60 g of melamine resin ® MAPRENAL MF650 (Hoechst) and 2.50 g of dispersant ® DISPERBYK 160 (Byk Chemie) are dispersed together for 90 minutes using a shaker machine (total coating material 150 g, 5% pigment). |

27.69 g of the masstone coating material obtained in this way are mixed, for the basecoat finish, with 17.31 g of Al stock solution (8% strength) comprising

| 12.65 g | of ® SILBERLINE SS 3334AR, 60% (Silberline Ltd.) |
| 56.33 g | of CAB solution (as composition above) |
| 20.81 g | of polyester resin ® DINAPOL H700 |
| 2.60 g | of melamine resin ® MAPRENAL MF650 and |
| 7.59 g | of ® SOLVESSO 150* | and the mixture is applied by spraying (wet film thickness about 20 gm) to an aluminium panel. After an evaporation time of 30 minutes at room temperature, a thermosetting acrylic varnish comprising

| 29.60 g | of acrylic resin ® URACRON 2263 XB, 50% in xylene/butanol (Chem. Fabrik Schweizerhalle), |
| 5.80 g | of melamine resin ® CYMEL 327, 90% in isobutanol, |
| 2.75 g | of butylglycol acetate, |
| 5.70 g | of xylene, |
| 1.65 g | of n-butanol, |
| 0.50 g | of silicone oil, 1% in xylene, |
| 3.00 g | of light stabilizer ® TINUVIN 900, 10% in xylene (Ciba), and |
| 1.00 g | of light stabilizer ® TINUVIN 292, 10% in xylene (Ciba) | is applied (wet film thickness about 50 gm) by spraying as a topcoat finish. After evaporation at room temperature for a further 30 minutes the coating is baked at 130° C. for 30 minutes.

Example 4: 0.6 g of the pigment prepared according to Example 1b is mixed with 67 g of polyvinyl chloride, 33 g of dioctyl phthalate, 2 g of dibutyltin dilaurate and 2 g of titanium dioxide and the mixture is processed on a roller mill at 160° C. for 15 minutes to give a thin sheet. The red PVC sheet produced in this way is distinguished by very good fastness properties.

Example 5: Replacement of the pigment used in Example 3 by the same quantity of the pigment prepared according to Example 2 produces, after processing in accordance with Example 3, a highly saturated orange coating material having excellent fastness properties.

Example 6: Replacement of the pigment used in Example 4 by the same quantity of the pigment prepared according to Example 2 produces, after processing in accordance with Example 4, a highly saturated orange coloration in PVC having excellent fastness properties.

What is claimed is:

1. A diketopyrrolopyrrole of the formula

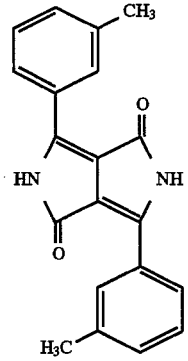
(I)

a) in its β-modification, whose X-ray diffraction pattern is characterized by the following diffraction lines

| Interplanar spacings (d values in Å) | double glancing angle (2Θ) | relative intensity |
|---|---|---|
| 13.7172 | 6.44 | 100 |
| 5.4273 | 16.32 | 44 |
| 4.7045 | 18.85 | 18 |
| 4.5517 | 19.49 | 31 |
| 4.3463 | 20.42 | 22 |
| 4.1056 | 21.63 | 11 |
| 3.4241 | 26.00 | 70 |
| 3.2844 | 27.13 | 31 |
| 3.0960 | 28.81 | 16 |
| 3.0625 | 29.14 | 18 | or b) in its γ-modification, whose X-ray diffraction pattern is characterized by the following diffraction lines

| Interplanar spacing (d values in Å) | double glancing angle (2Θ) | relative intensity |
|---|---|---|
| 11.1386 | 7.93 | 100 |
| 6.9644 | 12.70 | 19 |
| 4.6733 | 18.98 | 10 |
| 4.3887 | 20.22 | 12 |
| 4.0033 | 22.19 | 19 |
| 3.6052 | 24.67 | 84 |
| 3.3749 | 26.39 | 12 |
| 3.2335 | 27.56 | 49 |
| 2.9053 | 30.75 | 13. |

2. A diketopyrrolopyrrole according to claim 1 in its γ-modification.

* * * * *